(12) United States Patent
Dalrymple

(10) Patent No.: US 6,857,196 B2
(45) Date of Patent: Feb. 22, 2005

(54) METHOD AND APPARATUS FOR MEASURING A INTRACORPORAL PASSAGE IMAGE

(76) Inventor: Robert Dalrymple, 6 Thomas Point Ct., Baltimore, MD (US) 21234-1352

( * ) Notice: Subject to any disclaimer, the term of this patent is extended or adjusted under 35 U.S.C. 154(b) by 0 days.

(21) Appl. No.: 10/694,948

(22) Filed: Oct. 29, 2003

(65) Prior Publication Data

US 2004/0216317 A1 Nov. 4, 2004

Related U.S. Application Data

(63) Continuation of application No. 29/180,690, filed on Apr. 30, 2003, now Pat. No. Des. 496,596.

(51) Int. Cl.$^7$ ................................................ G01B 3/14
(52) U.S. Cl. ........................................... 33/512; 33/562
(58) Field of Search .................... 33/512, 562, 563, 33/566, 1 B, 555.2; 382/128, 132, 209; 128/922

(56) References Cited

U.S. PATENT DOCUMENTS

| | | | |
|---|---|---|---|
| 1,409,723 A | * | 3/1922 | Stanley ........................ 33/1 B |
| 2,896,333 A | * | 7/1959 | Kivela ........................ 33/555.2 |
| 3,812,842 A | | 5/1974 | Rodriguez |
| 4,630,375 A | | 12/1986 | Spolyar |
| 4,860,331 A | | 8/1989 | Williams et al. |
| 5,216,700 A | | 6/1993 | Cherian |
| 5,253,427 A | * | 10/1993 | Bartlett ........................ 33/555.2 |
| 5,400,513 A | | 3/1995 | Duffield |
| 5,501,020 A | * | 3/1996 | Welt ........................ 33/555.2 |
| 5,822,875 A | | 10/1998 | Feldner |
| 5,970,119 A | | 10/1999 | Hofmann |
| 6,061,920 A | | 5/2000 | McMorrow |
| 6,097,978 A | | 8/2000 | Demarais et al. |
| 6,366,362 B1 | * | 4/2002 | Butterfield et al. ......... 382/209 |
| 6,563,942 B2 | * | 5/2003 | Takeo et al. ................. 382/209 |
| 6,687,386 B1 | * | 2/2004 | Ito et al. ..................... 382/209 |

* cited by examiner

*Primary Examiner*—Christopher W. Fulton
(74) *Attorney, Agent, or Firm*—Cahn & Samuels, LLP.

(57) ABSTRACT

A medical measuring apparatus for measuring a lumen of an intracorporeal passage as it appears in an image wherein the apparatus preferably includes a measuring adjunct and an object to image retainer. The measuring adjunct preferably includes at least one geometric figure outline having a border formed by a portion of the measuring adjunct such that an aperture having a geometric shape is defined for measuring the lumen of the intracorporeal passage. The at least one geometric figure outline preferably includes a corresponding measurement specification (for example, in the metric system). In at least one embodiment, the at least one geometric figure outline is preferably utilized to measure an occlusion associated with the intracorporeal passage (for example, a renal tumor). The object to image retainer is for housing the measuring adjunct and compensates for a magnification ratio relating to the intracorporeal passage and the intracorporeal passage as it appears in the image.

13 Claims, 8 Drawing Sheets

METHOD AND APPARATUS FOR MEASURING A INTRACORPORAL PASSAGE IMAGE

This application is a continuation of U.S. Design Patent application Ser. No. 29/180,690, filed Apr. 30, 2003 now U.S. Pat. No. D. 496,596.

FIELD OF THE INVENTION

The present invention relates to medical surgical procedures, and more specifically to vascular surgery.

BACKGROUND OF THE INVENTION

Vascular disease is one of the leading causes of morbidity and mortality in the United States. For example, a common type of vascular disease is known as Atherosclerosis, a vascular disease that occurs in artery segments (for example, in the carotid artery, the renal arteries, and peripheral arteries of the limbs). Atherosclerosis (also known as hardening of the arteries) is a progressive, degenerative arterial disease that leads to occlusion of affected blood vessels, thereby reducing vessel patency, and hence, blood flow through the vessels. For example, plaques such as fatty substances, cholesterol, calcium and/or fibrin may build in the inner lining of arteries, thereby causing an occlusion that results in narrowing of the lumen of these blood vessels.

As arteries are internal, special procedures must be employed to locate the occlusion in the arteries. For example, a procedure known as catheterization is typically utilized in an attempt to locate a blocked blood vessel such as an artery. Differently shaped catheters may be introduced into the femoral artery, for example, by passing them through a sheath to locate the blocked artery, to measure the amount of oxygen in the blood, or to view blood flow, for example. Viewing blood flow is accomplished by a procedure known as angiography (also known as arteriography). The procedure involves injecting dye through a catheter while a series of rapid X-ray images is recorded. In this fashion, "movies" can be made to view blood flow.

Regardless, however, of the purpose for conducting a catherization procedure (for example, to determine the amount of oxygen in blood, to view blood flow, or to locate and unblock an artery), selection of the proper catheter size/dimension for a particular catherization procedure is a critical step. If a catheter having too large of a size (often referred to in French scale, 3F=1 mm) is inserted into a blood vessel, a variety of complications may occur. Complications include leakage around the catheter, encrustation, irritation, and infection. A serious type of complication can result from damage to the blood vessel and bleeding occasioned thereby. Extensive bleeding can lead to a host of various complications such as embolisms and aneurisms, etc., which can result in strokes or heart attacks. An oversized catheter may also perforate the wall of a proximate organ (for example, a kidney, in a renal catherization procedure). Further, sudden blockage of an artery may occur if the employed catheter is too large. This can also lead to a stroke, for example, and in some cases, utilizing a catheter of an inappropriate size may be fatal to a patient.

Thus, a significant amount of care must be taken to ensure that a properly sized catheter is selected for insertion into a particular vessel. Some medical professionals base catheter selection on guiding formulas developed by using attributes of patients such as height and age. These formulas, however, do not typically take into consideration the specifics of the particular patient being subjected to the intracorporeal surgical procedure. As a result, an incorrectly-sized catheter may be chosen.

In addition to using the above described attribute-based method for determining size of a vessel in an image, medical professionals attempt to determine vessel size by relying on experience to judge size of the vessel. This approach can lead to inaccurate determinations.

Another method for determining size of objects in images uses a "marker" catheter having a pair of radio-opaque markers spaced approximately two centimeters apart with a direct arithmetic proportional calculation based upon observed apparent lengths. This method, too, has disadvantages. First, it is often difficult to include both the markers and the anatomic region of interest on the same image during a procedure. Secondly, some conventional marker catheters do not have any mechanisms for ensuring that the line extending between the two markers is perpendicular to the image beam. This causes the image beam to foreshorten the apparent distance between the two markers on the image which can result in an inaccurate determination of the size of the anatomic structure in question. Thirdly, some conventional marker catheters are designed exclusively for intravascular use and ignore biliary and bronchial applications. Finally, a medical professional may begin a procedure with an unmarked catheter and may not realize until the procedure is already under way that it is desirable to measure the size of a structure. In such a case, it can be difficult, time-consuming, and expensive to exchange an unmarked catheter for a marked catheter.

A number of other methods have been developed in the prior art for determining the size of objects in images. For example, U.S. Pat. No. 2,819,526, issued to Brown, Jr., describes a calculator for use with X-ray images for determining object size in images. U.S. Pat. No. 4,974,164, issued to Lewis et al., describes a digital measuring and proportioning instrument comprising a hand-held microcomputer based ruler-like measuring and calculating instrument that is particularly adapted for measuring the sizes of objects in the field of graphic arts. In addition, U.S. Pat. No. 5,170,570, issued to Mays, Jr., describes a hand, finger, and joint measuring gauge for measuring objects. While the foregoing prior art devices and methods have proved useful, they suffer from a number of disadvantages. For instance, some are complex to use. Others are costly or have an inadequate measurement range.

Therefore, what is needed is an apparatus and method for assisting a medical professional with a more accurate selection of a properly sized catheter to be used in a vessel. Such an apparatus should allow a medical professional to more precisely measure the particular vessel at issue to determine a catheter size best fitted for the vessel.

SUMMARY OF THE INVENTION

It is an object of the present invention to overcome problems of the prior art.

An objective of the present invention is to provide for a more precise and accurate selection of medical catheters for vascular surgical procedures.

Another objective of the present invention is to minimize use of improperly sized/dimensioned medical catheters.

An advantage of the invention is that it can be used in conjunction with a variety of imaging techniques.

Another advantage of the invention is that it provides for an accurate selection of a medical catheter to be inserted into an intracorporeal passage (that is, a vessel).

Yet another advantage of the invention is that obliquely disposed intracorporeal passages in an image can be more accurately measured.

Yet another advantage of the invention is that it provides compensation for object to image ratio.

The present invention is a medical measuring apparatus and method for using the same for more accurately determining an appropriately sized/dimensioned catheter for a target intracorporeal passage into which the catheter is to be inserted. In short, the present invention contemplates substituting for "eyeballing" of images in connection with measuring intracorporeal passages.

In particular, the medical measuring apparatus measures a lumen of an intracorporeal passage as it appears in an image and preferably includes a measuring adjunct and an object to image retainer.

The measuring adjunct preferably includes at least one geometric figure outline having a border formed by a portion of the measuring adjunct such that an aperture having a geometric shape is defined for measuring the lumen of the intracorporeal passage. The at least one geometric figure outline preferably includes a corresponding measurement specification (for example, in the metric system). In at least one embodiment, the at least one geometric figure outline may be utilized to measure an occlusion associated with the intracorporeal passage (for example, a renal tumor).

The object to image retainer is for housing the measuring adjunct and preferably has a calibrated height adjustment means for adjusting height of the measuring adjunct such that the measuring adjunct lies between the height adjustment means. The object to image retainer compensates for a magnification ratio relating to the intracorporeal passage and the intracorporeal passage as it appears in the image.

In at least one embodiment, the measuring adjunct of the medical measuring apparatus described above preferably includes a plurality of the geometric figure outlines described above. The shape of each geometric figure outline, however, may vary according to its use. For example, at least one of the geometric figure outlines included in the plurality of geometric figure outlines preferably includes an aperture having a geometric shape defined for measuring the lumen of the intracorporeal passage. At least one of the geometric figure outlines preferably includes a circular-shaped aperture for measuring a cross section of the intracorporeal passage image. In the embodiment of the invention where occlusions may be measured, at least one of the geometric figure outlines preferably includes a square-shaped aperture for measuring an occlusion of the intracorporeal passage. The measuring adjunct also preferably includes at least one geometric figure outline including a slot-like aperture for measuring an occlusion associated with the intracorporeal passage. In addition to the above described geometric figure outlines, at least one geometric figure outline including a step-like aperture for measuring distance between walls of the intracorporeal passage as the walls appear in the image is preferably included in the measuring adjunct.

In a particularly advantageous aspect of the invention, at least one geometric figure outline is provided for allowing a medical professional to accurately determine size/dimension of a lumen of an obliquely disposed (foreshortened) passage in an image.

A medical professional operates the medical measuring apparatus by placing the measuring adjunct of the apparatus in the object to image retainer. The height adjustment means of the retainer allows the medical professional to minimize object to image distortion. The medical professional then places the apparatus in the range of the imaging source field (for example, a standard fluoroscopic imaging source field) such that the apparatus and the intracorporeal passage appear in the image. Next, the medical professional preferably aligns a geometric figure outline in the measuring adjunct with the intracorporeal passage as the passage appears in the image such that the lumen of the intracorporeal passage can be measured to more precisely determine selection of a catheter having a size compatible with the vessel.

When a particular geometric figure outline of the measuring adjunct matches the lumen of the intracorporeal passage, the measurement specification corresponding to the particular geometric figure outline is noted. The medical professional can then select a catheter having a size/dimension (for example, diameter) indicated by the measurement specification. If, however, the selected geometric figure outline does not match the vessel of interest, the medical professional chooses another geometric figure outline and determines whether there is a match between the selected geometric figure outline and the vascular vessel of interest. The visual approximation procedure described above continues until a match is discovered between one of the geometric figure outlines and the vascular vessel of interest. Obtaining a match and, thus, a catheter of proper size is vital in vascular surgical procedures, as it minimizes or prevents complications that can arise from employing a catheter with an incorrect size/dimension.

Definitions

As used herein, the term "image" generally refers to any displayed capture of an object, whether still or real-time, that occurs through procedures such as photogrammetry, photo-intelligence, X-ray procedures, Cat Scan procedures, Ultra-Sound procedures, PET Scan Tomographic procedures, CRT procedures, radiography or any other procedure used to capture an object.

As used herein, the term "Digital Subtraction Angiography" generally describes a method for showing contrast-filled intracorporeal passages without any interfering background.

As used herein, the term "imaging source" generally refers to any energy source capable of producing an image such as a photogrammetry source, photo-intelligence source, X-ray source, Cat Scan source, Ultra-sound source, PET Scan Tomographic source, CRT source, radiography source, or any other source used to capture an object to thereby produce an image of the object.

As used herein, the term "intracorporeal passage" generally refers to an intracorporeal structure for conveying body fluid such as a blood vessel (for example, a carotid artery, a renal artery, or a peripheral artery), a uretha, or a bile duct.

As used herein, the term "percutaneous" describes any procedure that is performed through the skin.

As used herein, the term "intravascular" means within a blood vessel (for example, an artery, vein, or capillary).

As used herein, the term "fluoroscopy" generally refers to any medical procedure for observing the internal structure of the body.

As used herein, the term "object" refers to a structure undergoing an imaging procedure.

As used herein, the term "magnification ratio" generally refers to the ratio of the image dimensions to the object dimensions.

As used herein, the term "intracorporeal passage image" refers to an intracorporeal passage as it appears in an image.

As used herein, the term "obliquely disposed" generally describes a vessel (for example, an artery, vein, or capillary) appearing in an image at an angle that is not normal to the image.

Given the following description of the drawings, the medical measuring apparatus of the present invention should become evident to a person of ordinary skill in the art.

BRIEF DESCRIPTION OF THE DRAWINGS

Like reference numerals in the figures represent and refer to the same element or function throughout.

DETAILED DESCRIPTION OF THE INVENTION

Figure 1:
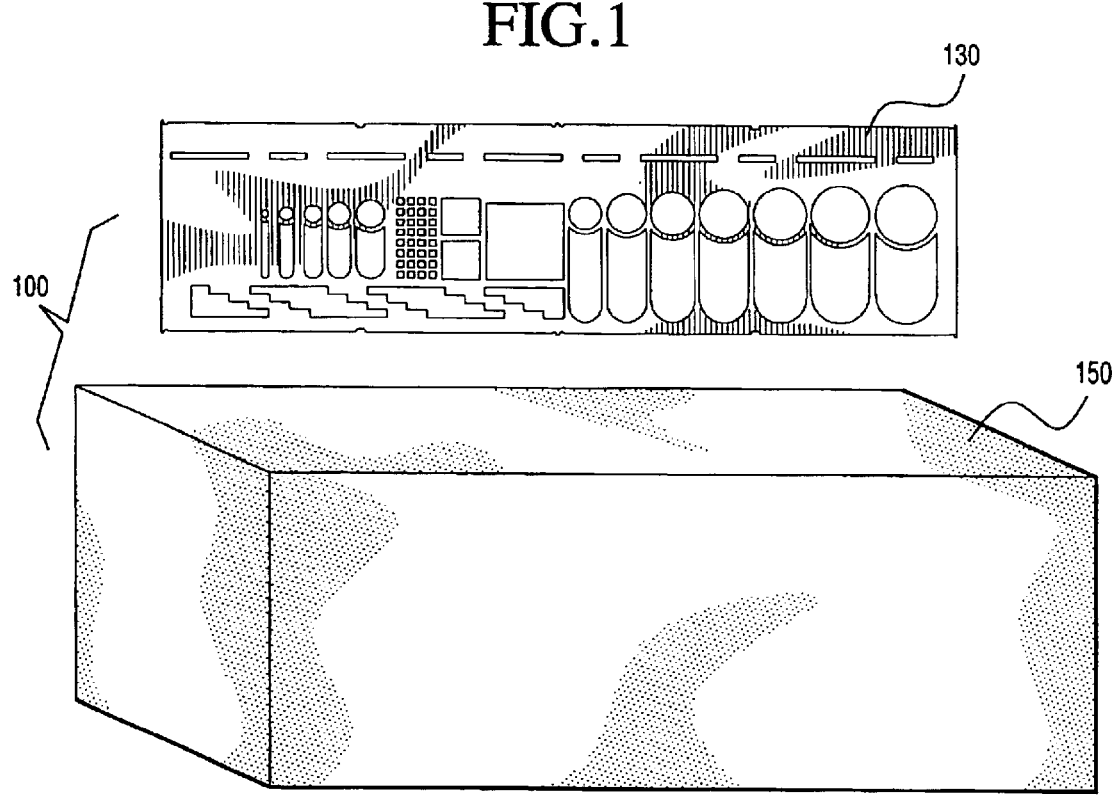
FIG. 1 is an illustration of an exemplary medical measuring apparatus including a measuring adjunct and an object to image retainer in accordance with an embodiment of the present invention.

FIG. 1 illustrates the exemplary medical measuring apparatus 100. The apparatus 100 preferably includes a measuring adjunct 130 and an object to image retainer 150 in accordance with the illustrated embodiment of the present invention. In the embodiment depicted in FIG. 1, the object to image retainer 150 is a pad. As will be described below, however, in alternative embodiments, the object to image retainer 150 is not necessarily a pad. It should also be noted that in at least one embodiment of the invention, the object to image retainer 150 may be a mechanically/hydraulically controlled device for adjusting the height of the measuring adjunct 130. In another embodiment, the object to image retainer 150 may not be present. In such an embodiment, the medical measuring apparatus 100 includes only the measuring adjunct 130.

In the embodiment of the invention depicted in FIG. 1, a medical professional operates the medical measuring apparatus 100 preferably by placing the measuring adjunct 130 into the object to image retainer 150 (for example, a pad, as depicted in FIG. 1) such that the measuring adjunct 130 and the top of the object to image retainer 150 are generally perpendicularly disposed (for example, along the Y-axis), as will be described further below. In at least one embodiment of the present invention, the measuring adjunct 100 is placed atop the object to image retainer 150. Regardless of whether the measuring adjunct 100 is placed atop the object to image retainer 150 or in the object to image retainer 150, the retainer 150 including the adjunct 130 is preferably placed in near proximity, as visually estimated, to the target (for example, a vascular vessel such as an artery (not shown in FIG. 1)). An imaging process is then conducted, thereby allowing both the vascular vessel and the adjunct 130 to undergo imaging. Interrelation between the measuring adjunct 130 and the object to image retainer 150 and operation of the medical measuring apparatus will be described herein in greater detail below.

Figure 2:
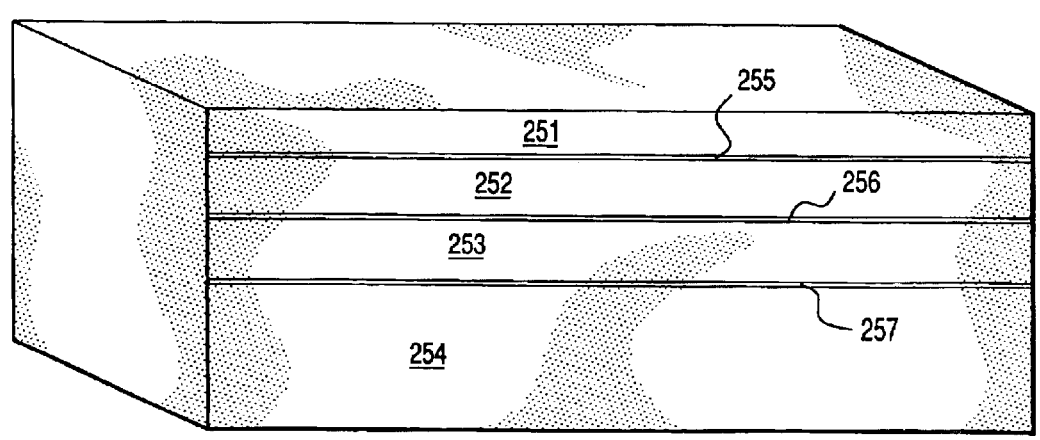
FIG. 2 is an illustration of an exemplary object to image retainer in accordance with an embodiment of the present invention.

FIG. 2 is an illustration of an exemplary object to image retainer 150 in accordance with an embodiment of the present invention. The object to image retainer 150 is preferably non-disposable and is comprised of foam covered with Latex or any other viable material suitable for enduring imaging procedures. The object to image retainer 150 preferably includes a plurality of adjacent layers 251, 252, 253, and 254. Each of the plurality of layers, which serves as height adjustment means, is preferably separated by one of a plurality of slits 255, 256, and 257. For example, layer 251 is preferably separated from layer 252 by slit 255. Similarly, layer 252 is preferably separated from layer 253 by slit 256. Finally, layer 253 is preferably separated from layer 254 by slit 257. The measuring adjunct 130 (shown in FIG. 1) is preferably inserted within one of the plurality of slits 255, 256, and 257 such that the measuring adjunct 130 and the layers are generally perpendicularly disposed (for example, perpendicular to the Y-axis), as will be described in detail in FIG. 3A. A medical professional determines the slit in which the measuring adjunct 130 is to be inserted according to a desired magnification ratio, as will be later described.

Figure 3A:
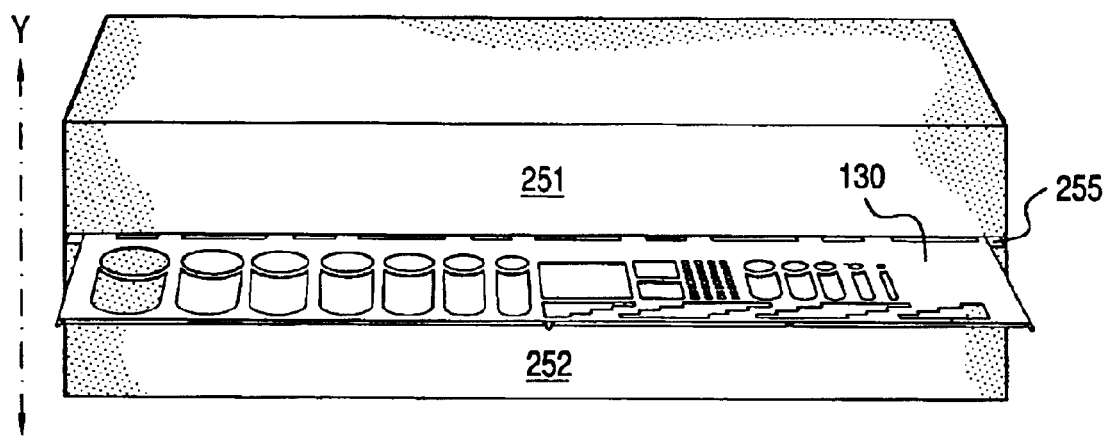
FIG. 3A is an illustration of an exemplary set of layers of the object to image retainer in FIG. 2 wherein the layers are separated by slits in accordance with an embodiment of the present invention.

FIG. 3A depicts the layers 251 and 252 of the object to image retainer 150 (shown in FIG. 2). The layers 251 and 252 are preferably separated by slit 255. The measuring adjunct 130 is preferably inserted horizontally into the slit 255 such that the measuring adjunct 130 lies atop the bottom-most layer of the two layers between which the measuring adjunct 130 resides, as depicted in FIG. 3A. In this configuration, the measuring adjunct 130 and the layers 251 and 252 are generally perpendicularly disposed (for example, along the Y-axis in FIG. 3A).

Figure 3B:
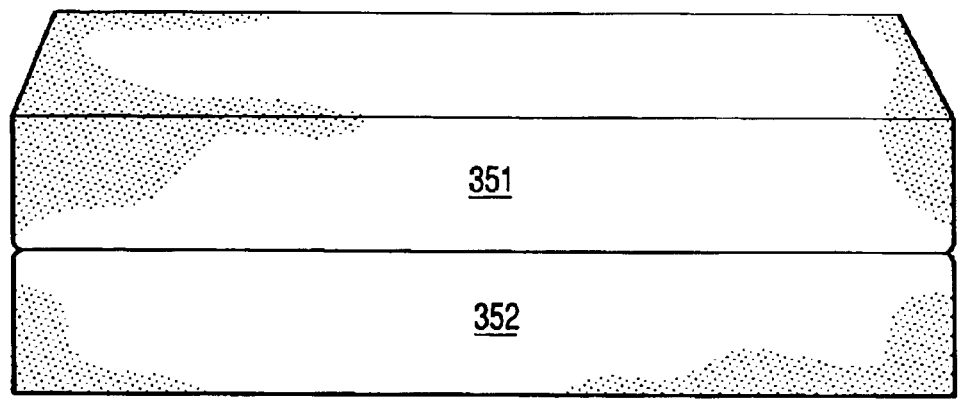
FIG. 3B is an illustration of an exemplary set of layers of the object to image retainer in FIG. 2 without slits in accordance with an embodiment of the present invention.

It should be noted, however, that in some embodiments, a layer may directly abut an adjacent layer such that the layers are not separated by a slit. For example, FIG. 3B depicts layers 351 and 352 of the object to image retainer 150 (shown in FIGS. 1 and 2). In FIG. 3B, however, the layers 351 and 352 rest directly atop one another (in an unattached state) before the measuring adjunct 130 is inserted between the two layers 351 and 352. The layers 351 and 352 are compressionable, however, as they are comprised of foam. Thus, although there is no slit in the embodiment shown in FIG. 3B, the measuring adjunct 130 (not shown in FIG. 3B) is preferably horizontally inserted between the compressionable layers 351 and 352 such that the measuring adjunct 130 lies horizontally sandwiched between the layers 351 and 352. The compressionable layers function to receive the measuring adjunct and frictionally engage and retain the measuring adjunct. It should be noted that the measuring adjunct 130 need not be fully inserted between the two layers 351 and 352. For example, only an edge of the measuring adjunct 130 needs to be lodged so as to be horizontally sandwiched between the two layers 351 and 352.

Figure 4:
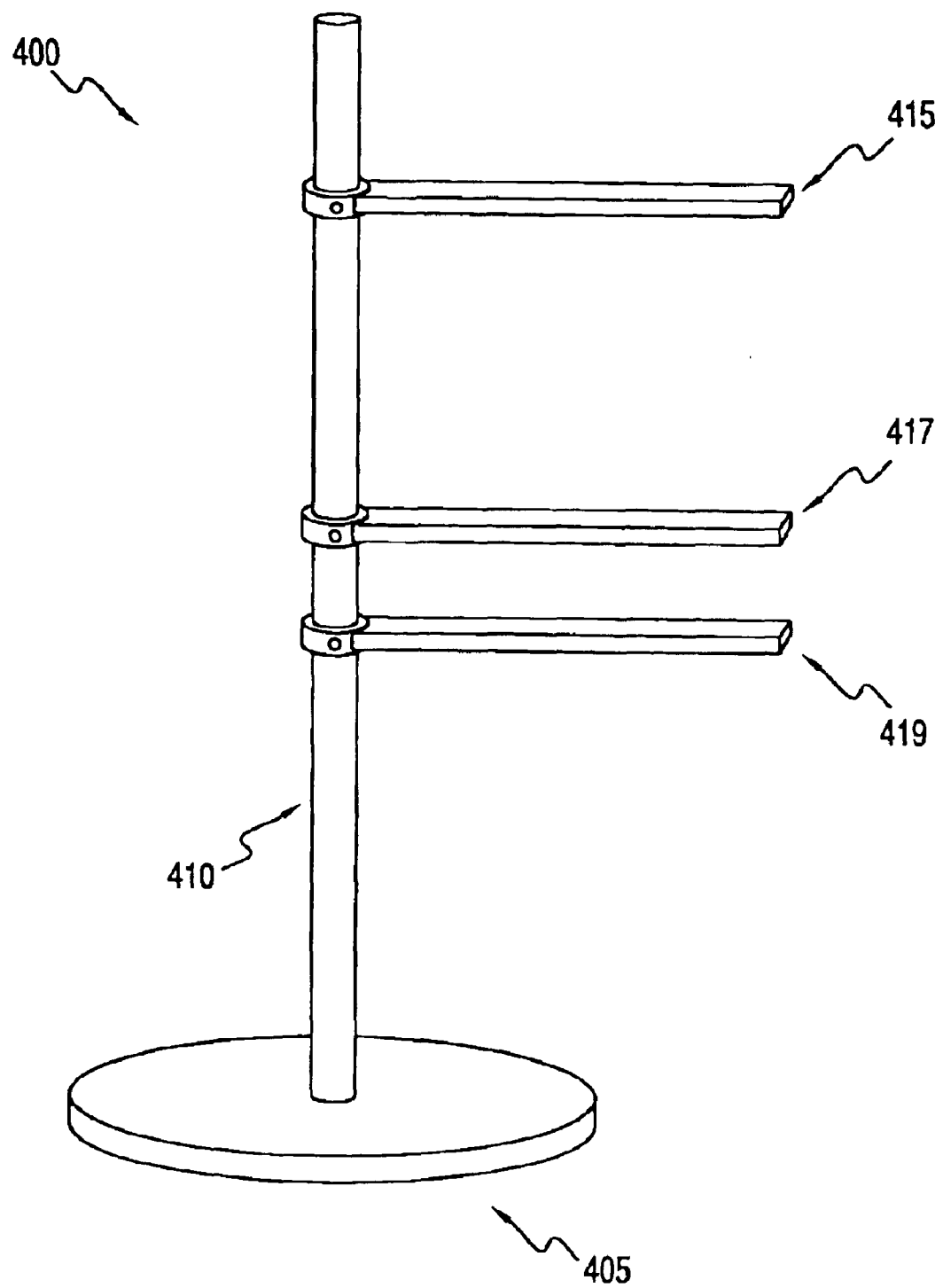
FIG. 4 is an illustration of an exemplary object to image height adjustment retainer in accordance with an alternative embodiment of the present invention.
Figure 5:
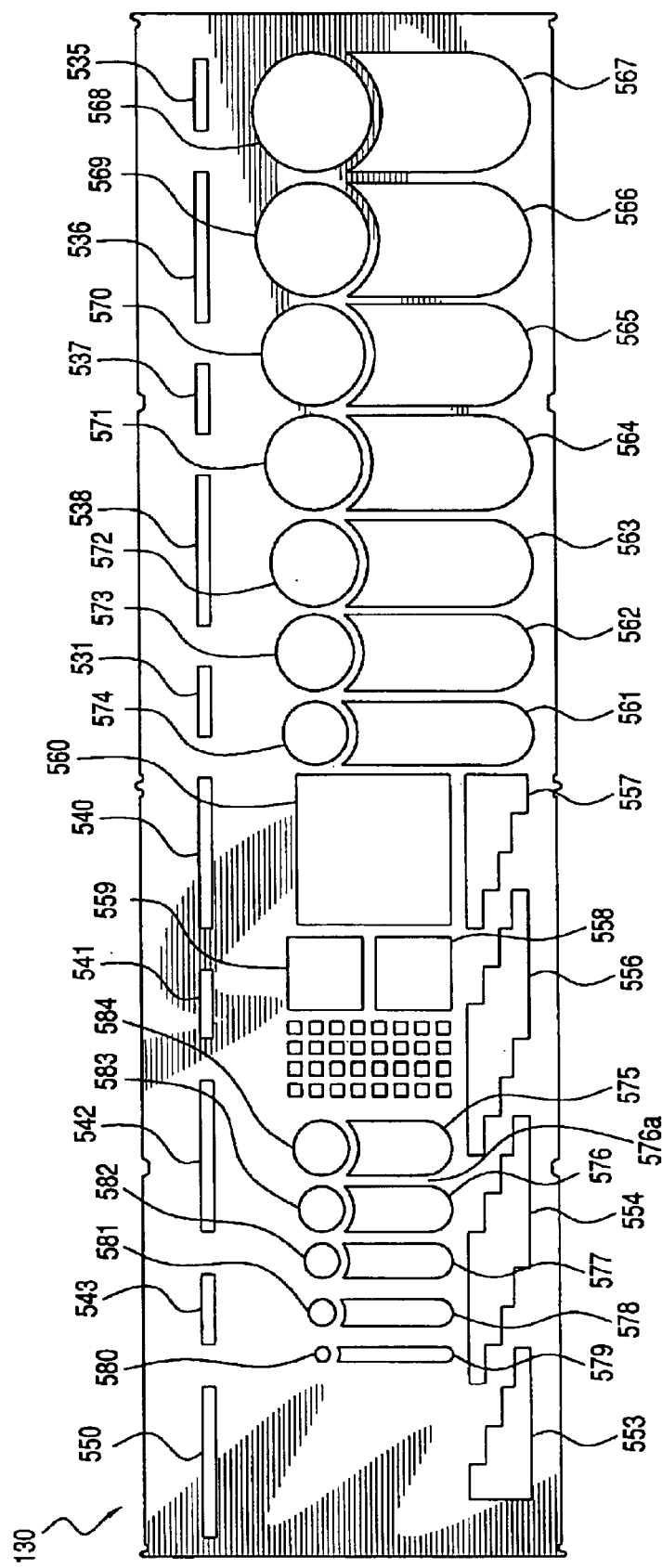
FIG. 5 is a top photographic view of an exemplary measuring adjunct in accordance with an embodiment of the present invention.
Figure 6:
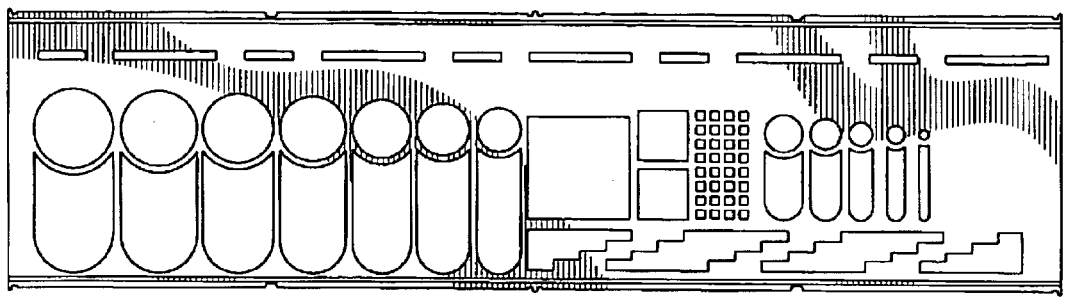
FIG. 6 is a bottom photographic view of an exemplary measuring adjunct in accordance with an embodiment of the present invention.
Figure 7:
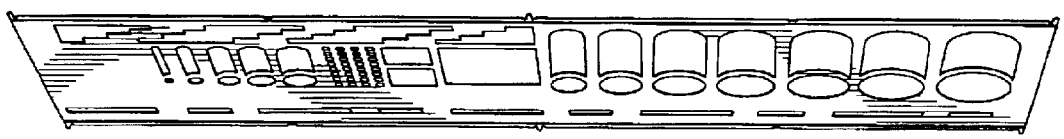
FIG. 7 is a perspective side photographic view of an exemplary measuring adjunct in accordance with an embodiment of the present invention.
Figure 8:
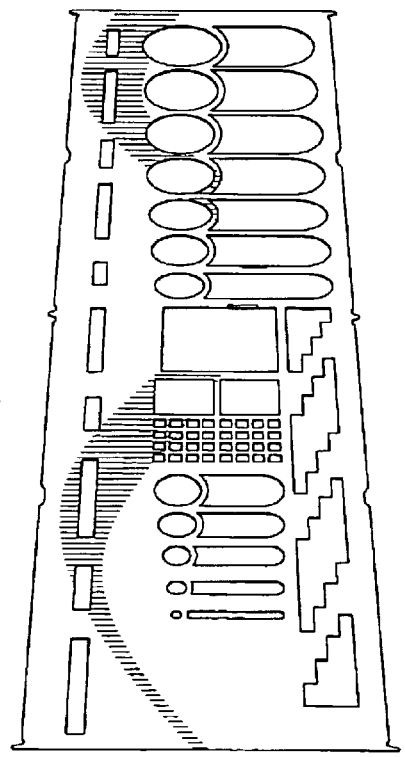
FIG. 8 is a perspective edge photographic view of an exemplary measuring adjunct in accordance with an embodiment of the present invention.

In FIG. 4, an alternative embodiment of the invention is shown. In FIG. 4, object to image height adjustment retainer 400 is comprised of a base 405, a stand 410 connected to the base 405, and a plurality of arms 415, 417, and 419 connected to the stand. The base 405, stand 410, and plurality of arms 415, 417, and 419 are preferably manufactured of a durable material such as a metal alloy and may be coated with other viable materials such as foam or latex.

The base 405 assists in stabilizing the object to image height adjustment retainer 400. The stand 410 is coupled to the base 405 and preferably allows the plurality of arms 415, 417, and 419 to serve as height adjustment means to allow the height of the measuring adjunct 130 (not shown in FIG. 4) to be adjusted to compensate for the magnification ratio. For example, the measuring adjunct 130 preferably rests on one of the plurality of arms 415, 417, and 419 according to a desired height of the adjunct 130. It should be noted that the distance between the plurality of arms 415, 417, and 419 may be varied. For example, the plurality of arms 415, 417, and 419 may be arranged such that they are separated by slits, similar to the slits depicted in the embodiment shown in FIG. 2. Other height adjustment structures for serving as the height adjustment means are contemplated for use with this invention so long as the structures provide the functionality of retaining the measuring adjunct at a user-selectable height adjustable by extendable means (for example, a piston structure, a gear structure such as a rack and pinion structure, a belt & pulley structure, or a dial structure). It should be noted that the height adjustment structures referenced above can be used to finely adjust the height of the measuring adjunct 130.

FIGS. 5–8 illustrate the measuring adjunct 130 of the medical measuring apparatus 100 for measuring a lumen of an intracorporeal passage (for example, vasculative) in which a catheter is to be inserted. The measuring adjunct 130 illustrated in FIGS. 5–8 enable a medical professional to accurately select a properly-sized catheter to be utilized in a particular vascular procedure, as will be described in more detail below.

The measuring adjunct 130 preferably includes a plurality of geometric figure outlines 531–584. The measuring adjunct 130 is preferably manufactured of a radio-opaque material such as brass, steel, stable and rigid polymer, copper, or any other viable material doped with boron for allowing the measuring adjunct 130 to be indisposable. The measuring adjunct 130 is preferably rectangular in shape.

Each geometric figure outline in the measuring adjunct 130 includes a border that is formed by a portion of the measuring adjunct 130 such that an aperture having a geometric shape is defined. The shape of each geometric figure outline preferably varies according to its use. For example, at least one of the geometric figure outlines included in the plurality of geometric figure outlines 531–584 preferably includes a circular-shaped aperture for measuring a cross-section of the intracorporeal passage image normal to the imaging plane (for example, the circular-shaped geometric figure outline 571 depicted in FIG. 5). In the embodiment of the invention where occlusions may be measured, at least one of the geometric figure outlines preferably includes a square-shaped aperture for measuring the occlusions (for example, the geometric figure outline 558). The measuring adjunct 130 also preferably includes at least one geometric figure outline including a slot-like aperture for measuring an occlusion associated with the intracorporeal passage (for example, the geometric figure outline 543). In addition to the above described geometric figure outlines, at least one geometric figure outline including a step-like aperture for measuring distance between walls of the intracorporeal passage is present (for example, the geometric figure outline 553).

Figure 9:
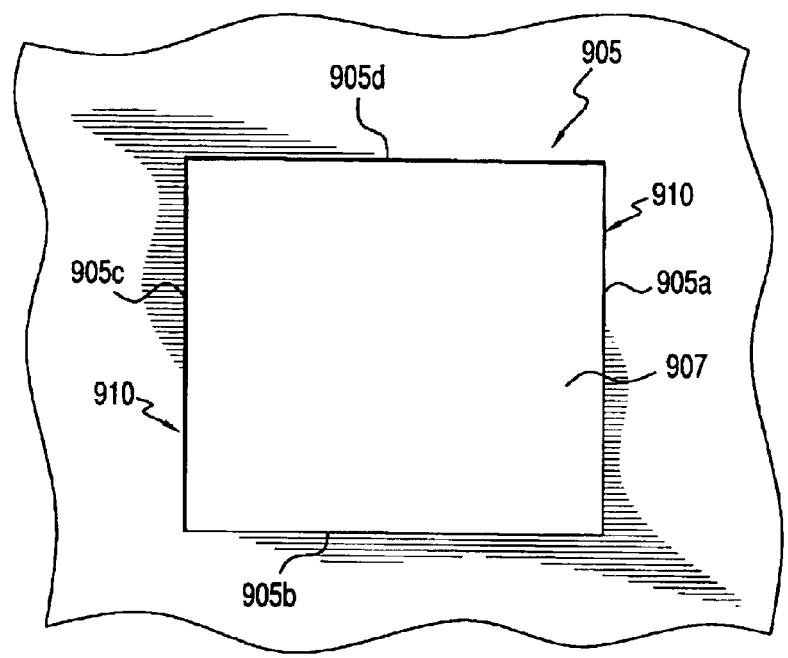
FIG. 9 is an illustration of a close-view perspective of an exemplary square-shaped geometric figure outline in accordance with an embodiment of the present invention.

In FIG. 9, the geometric figure outline 905 includes a border 910 which is a portion of the measuring adjunct 130 (shown in FIGS. 5–8). The border 910 of the geometric figure outline 905 defines an aperture 907 having the shape of a square.

It should be noted that no distinction is made herein between sides or edges of a geometric figure outline and a border of the geometric figure outline. As used herein, the term border refers to the actual portion of the measuring adjunct 130 that defines the perimeter of the corresponding aperture. Although geometric figure outline 905 is in the shape of a square which has four sides, namely 905a, 905b, 905c, and 905d, each side of the square-shaped geometric figure outline 905 is considered a part of the border 910. In other words, border 910 includes sides or edges 905a, 905b, 905c, and 905d of the square-shaped geometric figure outline 905. It should also be noted that a first geometric figure outline can share a border with another geometric figure outline. For example, referring to FIG. 5, geometric figure outline 576 shares a border 576a with geometric figure outline 575.

Figure 10:
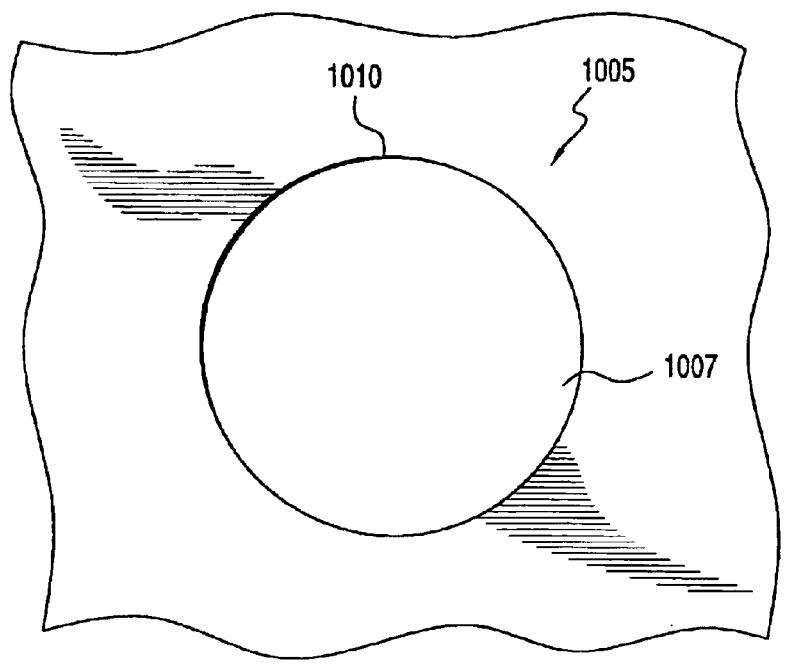
FIG. 10 is an illustration of a close-view perspective of an exemplary circular-shaped geometric figure outline in accordance with an embodiment of the present invention.

FIG. 10 depicts circularly shaped geometric figure outline 1005 which includes border 1010. Border 1010 defines aperture 1007. In a particular advantageous aspect of the invention (as will be further described below), at least one geometric figure outline is provided for allowing a medical professional to measure an obliquely disposed intracorporeal passage in an image (for example, geometric figure outlines 575–579). Operation of the measurement adjunct 130 will now be described.

As discussed above, the measurement adjunct 130 of the present invention provides a medical professional with enhanced precision to more accurately select a catheter to be inserted into a given vascular vessel. Selection of a properly sized catheter is vital in vascular surgery, as significant damage to a given vessel may occur, resulting in a variety of complications if an improperly sized catheter is used.

The measuring adjunct 130 of the present invention can be used in conjunction with vascular procedures such as Angiography or more particularly Digital Subtracted Angiography, for example. While described herein as associated with intravascular and vascular procedures, the present invention is not intended to be so limited. As previously described, Angiography requires the injection of a radiopaque substance known to those skilled in the art as a contrast agent or dye. A small tube is used to place the contrast agent into a particular vessel of interest (for example, an artery or vein). While the vessel contains this radiopaque material, it will block the beam (for example, a photogrammetry beam), and will cast a shadow of the injected vessel onto the image, as is known to those skilled in the art. For instance, Digital Subtracted Angiography or plagiography, for example, may be used to inject the contrast media in the vascular vessel to assist in determining the size of the lumen of the vessel. The image typically reveals the shape of the vessel of interest. As previously mentioned, the medical professional may wish to use a catheter to obtain an oxygen sample from the brain, for example. As the medical measuring apparatus 100 of the invention appears in the image in proximity to the vessel, a medical professional may easily and accurately visually approximate the size/dimension of the lumen of the vessel.

Figure 11:
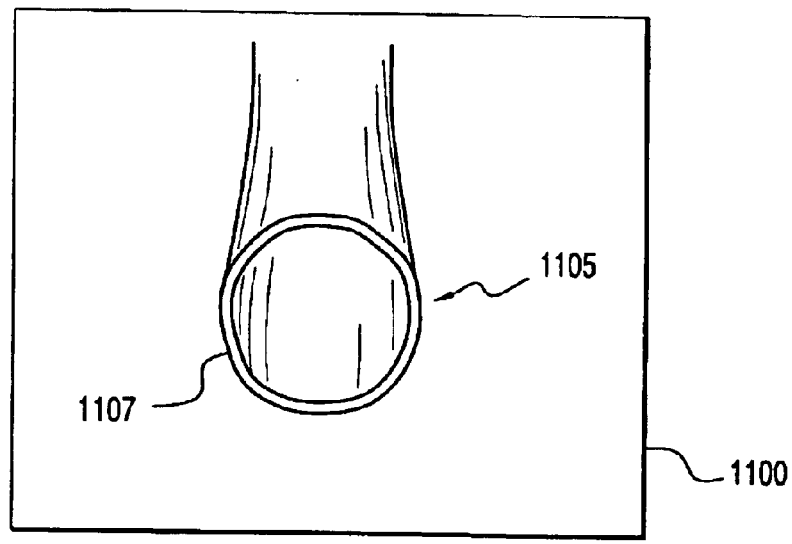
FIG. 11 is an illustration of a close-view perspective of an exemplary cross-section of an intracorporeal passage as it appears in an image.

FIG. 11 illustrates an image 1100 depicting a vascular vessel image, namely circularly-shaped artery image cross-section 1105. The edge of the cross-section 1105 is referred to herein as perimeter 1107. As shown in FIG. 11, the border 1107 represents the perimeter of the cross-section 1105. A medical professional desiring to measure the circumference/diameter of circularly-shaped cross-section 1105 may utilize the medical measuring apparatus of the present invention by approximating the size/dimension of the cross-section 1105. The medical professional visually compares one of the geometric figure outlines described above (for example, in the text regarding FIG. 5) with the image cross-section 1105. For example, the medical professional may determine that the image cross-section 1105 will require a catheter of a size corresponding to one of the geometric figure outlines 573 or 574 (shown in FIG. 5), for example. After determining which one of the geometric figure outlines 573 or 574 most closely "matches" (that is, the geometric figure outline that most closely approximates) the image cross-section 1105, the medical professional preferably notes the measurement specification corresponding to the particular geometric figure outline (that is, the "matching" geometric figure outline). Thus, the medical professional may then select a catheter with a proper size/dimension for the artery as depicted in the cross-section 1105 of the image 1100, and complications resulting from a catheter of improper size/dimension are minimized or prevented.

It should be noted that the medical measuring apparatus of the present invention may be used in conjunction with any of a number of computerized medical video image processing tools or a micrometer utilized to measure a vascular passage image. In such a situation, the resulting measurements from the medical measuring apparatus of the present invention and the measurements resulting from the computerized medical video image processing tools or the micrometer may be compared. The results from such a comparison may be used to obtain two-way verification, thereby enhancing the user's degree of confidence and minimizing the possibility of employing an improperly sized catheter to be inserted into a target vessel.

Figure 12:
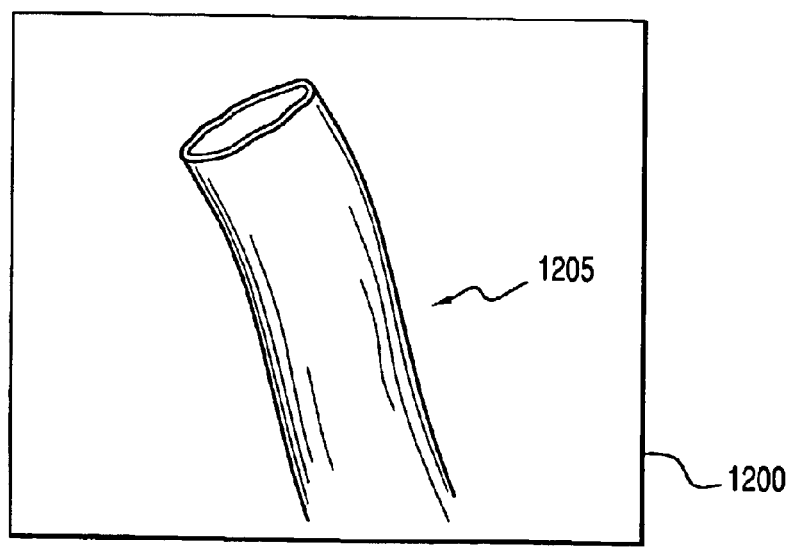
FIG. 12 is an illustration of an exemplary obliquely disposed (foreshortened) intracorporeal passage as it appears in an image.

As previously mentioned, in keeping with a particularly advantageous aspect of the present invention, size/dimension of obliquely disposed intracorporeal passages in an image may be determined by using the present invention. Referring to FIG. 12, if a medical professional desires to determine the size/dimension of the obliquely disposed artery 1205, as it appears in the image 1200, the medical professional utilizes the medical measuring apparatus of the present invention to determine which one of the geometric figure outlines 561–567 (shown in FIG. 5) most closely "matches" the obliquely disposed artery 1205 as it appears in the image 1200, using the visual approximation procedure described in the text regarding FIG. 11.

Figure 13:
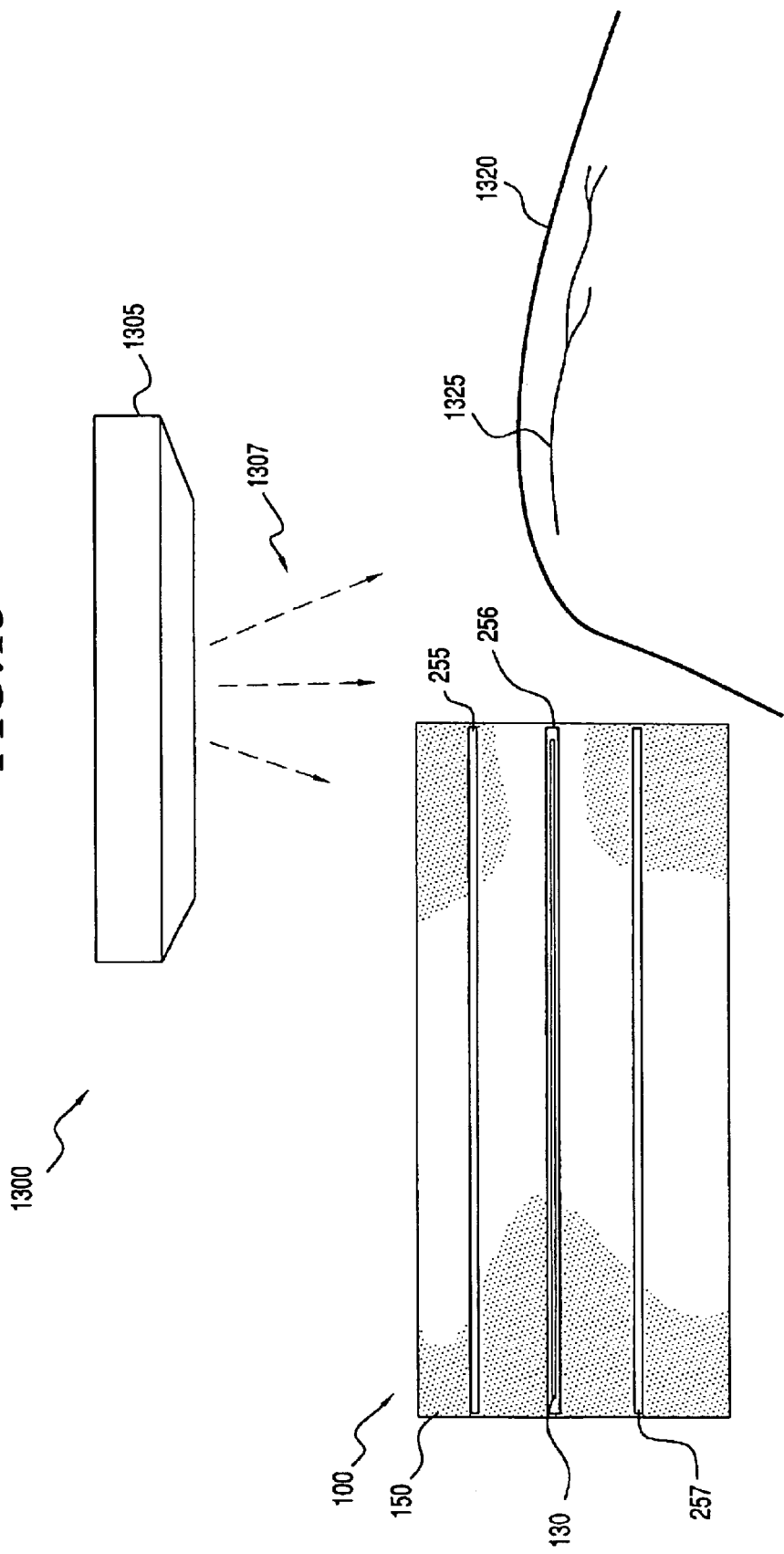
FIG. 13 is an illustration of an exemplary imaging scenario in which the medical measuring apparatus of the present invention is utilized.

FIG. 13 will now be used to describe how the present invention compensates for the magnification ratio during imaging procedures utilizing the medical measuring apparatus of the present invention. FIG. 13 depicts an imaging scenario 1300 including an imaging source 1305, the medical measuring apparatus 100 including the measuring adjunct 130 and the object to image retainer 150, and a limb 1320 including a peripheral artery 1325 (for example, the femoral artery). As described above, during operation of the imaging source 1305, a medical professional preferably injects contrast media into the peripheral artery 1325 to assist in accurately determining the size of the lumen of the peripheral artery 1325.

The medical professional then preferably places the object to image retainer 150 in a range of the imaging source field 1307 such that the object to image retainer 150 and the periphreral artery 1325 appear in the image resulting from the imaging source 1305. Next, the medical professional places the medical measuring adjunct 130 into one of the plurality of slits 255, 256, and 257 in the object to image retainer 150 to compensate for the relative height of the artery. For example, the peripheral artery 1325 depicted in FIG. 13 may have a diameter of 2 mm, but the peripheral artery image (that is, the peripheral artery, as it appears in the image resulting from the imaging source 1305) may have a diameter of 1.5 mm. Thus, a medical professional would know that the magnification ratio is approximately 1.3, and this must be taken into consideration when measuring the peripheral artery 1325 as it appears in the image. Thus, as one skilled in the art would recognize after being provided with the disclosure herein, the farther away from the camera (not shown in FIG. 13) the peripheral artery 1325 is (and the closer it is to the imaging source), the greater the magnification ratio. Finally, the medical professional preferably aligns a geometric figure outline in the medical measuring adjunct 130 with the peripheral artery 1325 depicted in the image such that the lumen of the peripheral artery 1325, as it appears in the image, can be measured to determine selection of a catheter having a size compatible with the peripheral artery 1325.

It should be noted that although specific vascular surgical procedures are described herein, they are used for purposes of exemplary illustration. It should be understood that the present invention is not to be limited to the specific procedures discussed herein. For example, in addition to having the capability to be employed in renal and carotid procedures, the present invention can be employed in other intracorporeal procedures (for example, neural and urethral procedures).

Those skilled in the art will appreciate that various adaptations and modifications of the above-described embodiments of the present invention can be configured without departing from the scope and spirit of the present invention. Therefore, it is to be understood that, within the scope of the appended claims, the invention may be practiced and constructed other than as specifically described herein.

I claim:

1. A medical measuring apparatus for measuring a lumen of a intracorporeal passage, as the intracorporeal passage appears in an image, comprising:

a measuring adjunct including at least one geometric figure outline having a border formed by a portion of said measuring adjunct such that an aperture having a geometric shape is defined for measuring the lumen of the intracorporeal passage, said at least one geometric figure outline having a corresponding measurement specification; and an object to image retainer for the measuring adjunct, said object to image retainer having calibrated height adjustment means for adjusting height of the measuring adjunct such that the measuring adjunct lies between the adjustment means, said object to image retainer for compensating for a magnification ratio relating to the intracorporeal passage and the intracorporeal passage as it appears in the image.

2. The medical measuring apparatus of claim 1, wherein said measuring adjunct is manufactured of a radio-opaque material selected from the group consisting of brass, steel, copper, metal alloys, and polymers, doped with boron.

3. The medical measuring apparatus of claim 1, wherein said object to image retainer includes a pad including a plurality of adjacent layers serving as the height adjustment means wherein each of said layers is separated by a slit, said slit for allowing the measuring adjunct to be inserted within, such that the measuring adjunct and the plurality of layers are perpendicularly disposed.

4. The medical measuring apparatus of claim 1, wherein said object to image retainer is a mechanically controlled device.

5. The medical measuring apparatus of claim 1, wherein said object to image retainer is a hydraulically controlled device.

6. The medical measuring apparatus of claim 1, wherein said geometric shape is for measuring an obliquely disposed intracorporeal passage, as the passage appears in an image.

7. The medical measuring apparatus of claim 1, wherein the object to image retainer includes a base, a stand connected to said base, and a plurality of arms connected to said stand.

8. A The medical measuring apparatus for measuring a lumen of an intracorporeal passage, as the passage appears in an image, said medical measuring apparatus comprising:

a measuring adjunct including
   a first geometric figure outline having a border formed by a portion of said measuring adjunct such that an aperture having a geometric shape is defined for measuring the lumen of the intracorporeal passage;
   a second geometric figure outline having a border formed by a portion of said measuring adjunct such that a circular-shaped aperture is defined for measuring a cross-section of the image of the intracorporeal passage;
   a measurement specification corresponding to said first geometric figure outline and said second geometric figure outline;
   wherein said medical measurina apparatus is manufactured of a radio-opague material selected from the group consisting of brass, steel, copper, metal alloys, and polymers, doped with boron; and an object to image height adjustment retainer for the measuring adjunct, said object to image height adjustment retainer having calibrated height adjustment means for selecting the height of the measuring adjunct to compensate for a magnification ratio relating to the intracorporeal passage and the intracorporeal passage as it appears in the image.

9. The medical measuring apparatus of claim 8, wherein said height adjustment means includes a pad including a plurality of adjacent layers serving as the height adjustment means wherein each of said layers is separated by a slit, said slit for allowing the measuring adjunct to be inserted within, such that the measuring adjunct and the plurality of layers are perpendicularly disposed.

10. A method for measuring the lumen of an intracorporeal passage depicted in an image, comprising:

placing a medical measuring apparatus including a measuring adjunct and an object to image height adjustment retainer in a range of an imaging source field such that said measuring apparatus and said intracorporeal passage appear in the image; and aligning a geometric figure outline in the measuring adjunct with the intracorporeal passage depicted in the image such that the lumen of the intracorporeal passage, as it appears in the image, can be measured to determine selection of a catheter having a size compatible with the intracorporeal passage.

11. The method of claim 10, further comprising, before said aligning step, inserting the measuring adjunct within one of a plurality of slits in said object to image height adjustment retainer to allow for a desired level of magnification of the image resulting from said imaging source.

12. The method of claim 11, wherein the inserting step includes partially inserting the measuring adjunct in said object to image retainer such that only an edge of the measuring adjunct resides between two layers included in the object to image retainer.

13. The method of claim 10, wherein said measuring adjunct is placed atop said object to image height adjustment retainer to allow for a desired level of magnification of the image resulting from said imaging source.

* * * * *